United States Patent
Houser

(10) Patent No.: US 6,936,024 B1
(45) Date of Patent: Aug. 30, 2005

(54) PERCUTANEOUS TRANSMYOCARDIAL REVASCULARIZATION (PTMR) SYSTEM

(75) Inventor: Russell A. Houser, 1787 Verdite St., Livermore, CA (US) 94550

(73) Assignee: Russell A. Houser, Livermore, CA (US)

( * ) Notice: Subject to any disclaimer, the term of this patent is extended or adjusted under 35 U.S.C. 154(b) by 587 days.

(21) Appl. No.: 09/632,519

(22) Filed: Aug. 4, 2000

Related U.S. Application Data

(60) Continuation-in-part of application No. 09/256,020, filed on Feb. 23, 1999, now Pat. No. 6,214,024, which is a division of application No. 08/899,490, filed on Jul. 19, 1997, now Pat. No. 5,876,369, which is a division of application No. 08/376,226, filed on Jan. 23, 1995, now Pat. No. 5,665,062.
(60) Provisional application No. 60/147,687, filed on Aug. 6, 1999.

(51) Int. Cl.[7] ............................................... A61B 17/20
(52) U.S. Cl. ......................................................... 604/22
(58) Field of Search ............................... 606/33, 41, 45, 606/46, 48, 50; 604/22

(56) References Cited

U.S. PATENT DOCUMENTS

| | | | | |
|---|---|---|---|---|
| 3,910,279 A | * | 10/1975 | Okada et al. ........... | 128/303.15 |
| 4,627,436 A | * | 12/1986 | Leckrone ................ | 128/303.1 |
| 4,638,802 A | * | 1/1987 | Okada .................... | 128/303.14 |
| 4,976,711 A | * | 12/1990 | Parins et al. ........... | 606/48 |
| 5,080,660 A | * | 1/1992 | Buelna .................... | 606/45 |
| 5,181,920 A | * | 1/1993 | Mueller et al. ......... | 606/159 |
| 5,415,656 A | * | 5/1995 | Tihon et al. ............ | 606/46 |
| 5,628,746 A | * | 5/1997 | Clayman ................. | 606/45 |

* cited by examiner

Primary Examiner—Manuel Mendez

(57) ABSTRACT

Percutaneous transmyocardial revascularizaton systems are disclosed for creating thin, linear incisions through the endocardium and partially into the myocardium. The systems mitigate the deficiencies of current approaches that position a distal tip channeling mechanism against the endocardial surface. The systems position a catheter body lengthwise along the endocardial surface and incorporate a cutting mechanism movable radially relative to the catheter body to create one or more elongate thin, linear incisions along one or more windows through the catheter body. Flexible support strands are used to urge each window into intimate contact with the endocardial surface. Each cutting element is adapted to protrude radially outward from the catheter body to contact tissue adjacent each window. The cutting mechanism incorporates a mechanical cutting element or an electrode designed to transmit direct current or radiofrequency energy into tissue to simultaneously cut and coagulate tissue. The catheter also can infuse a therapeutic agent directly into the incisions to encourage angiogenesis. The catheter also cuts thin, linear incisions capable of ablating arrhythmia substrates by disrupting electrical propagation through the affected myocardium.

29 Claims, 11 Drawing Sheets

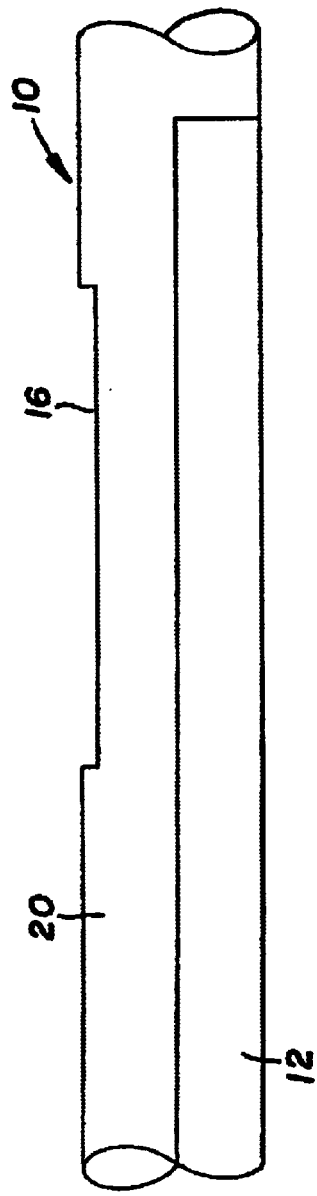
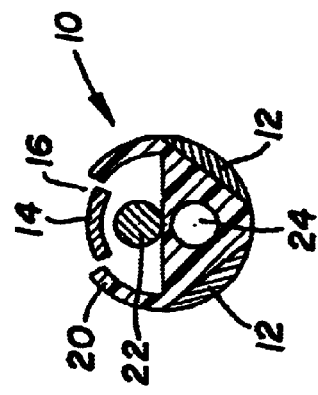
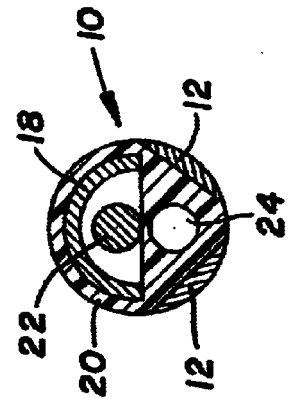
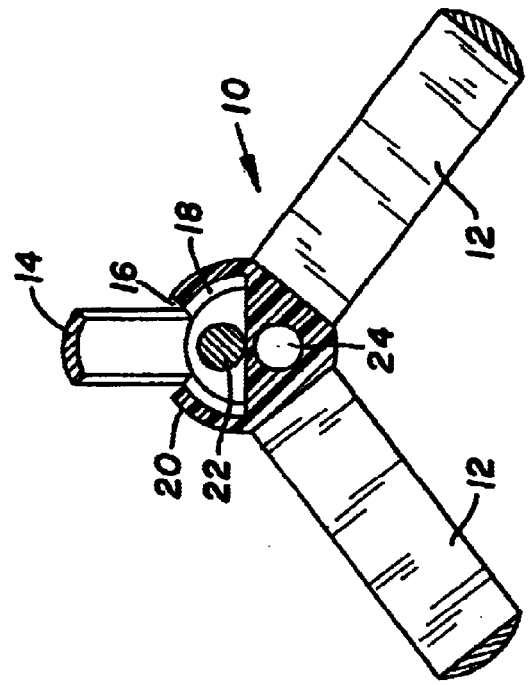

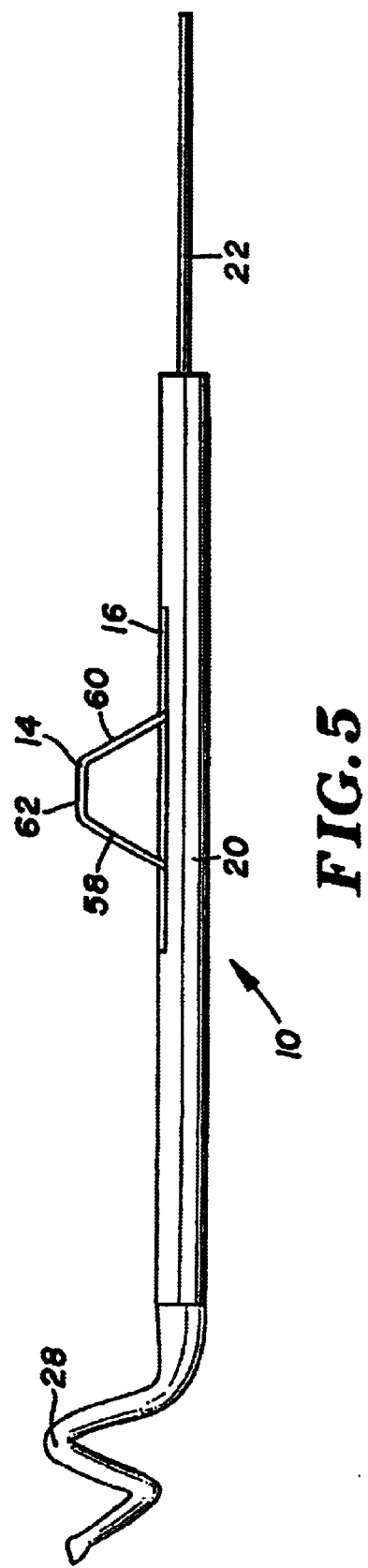

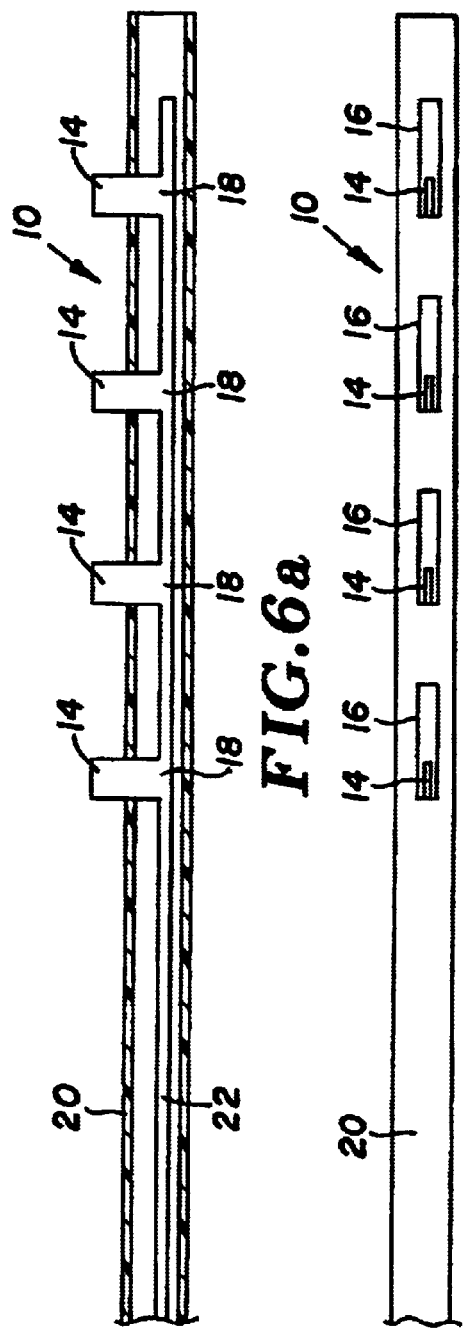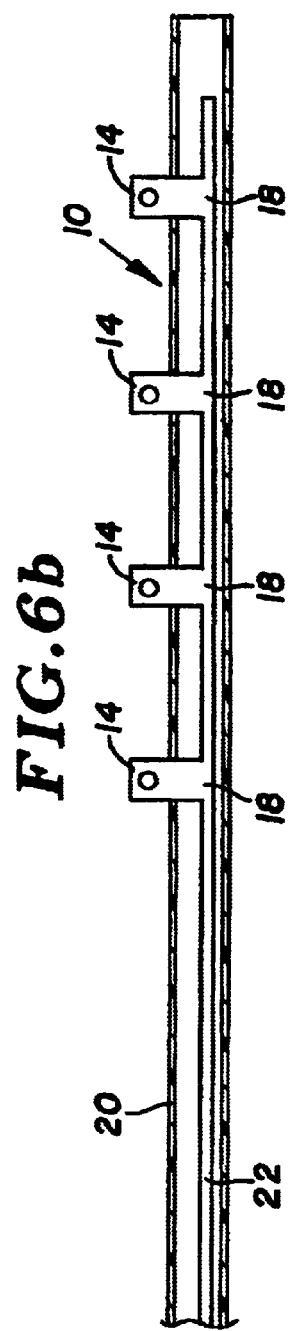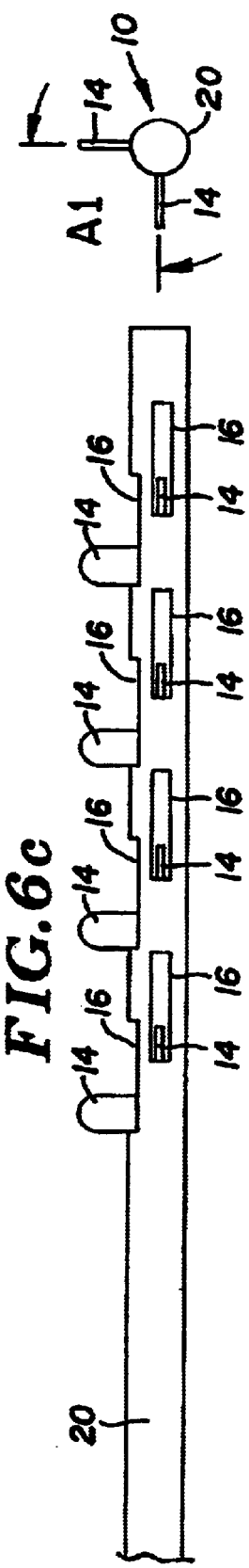
FIG.6a  FIG.6b  FIG.6c  FIG.6d  FIG.6e

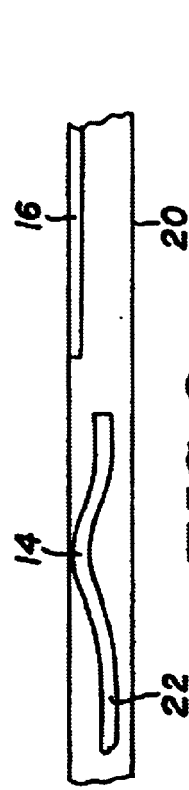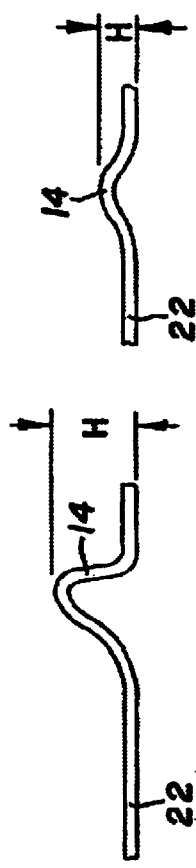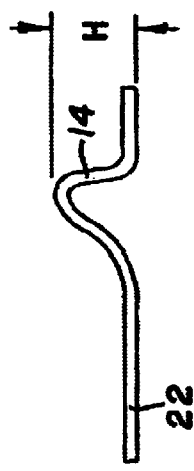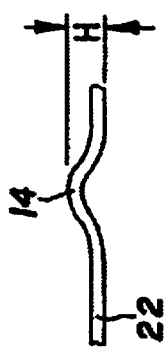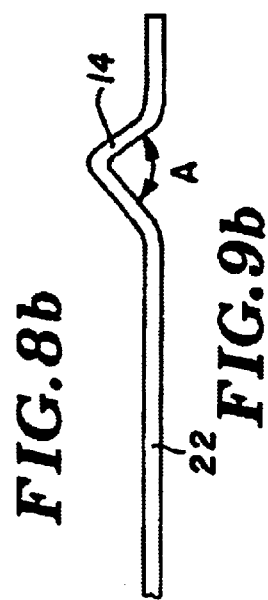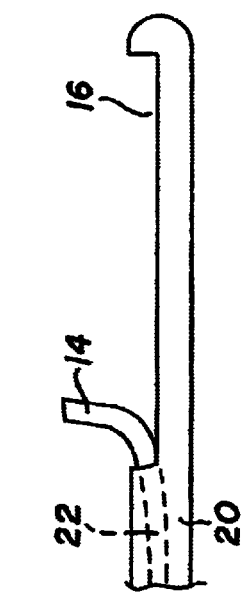

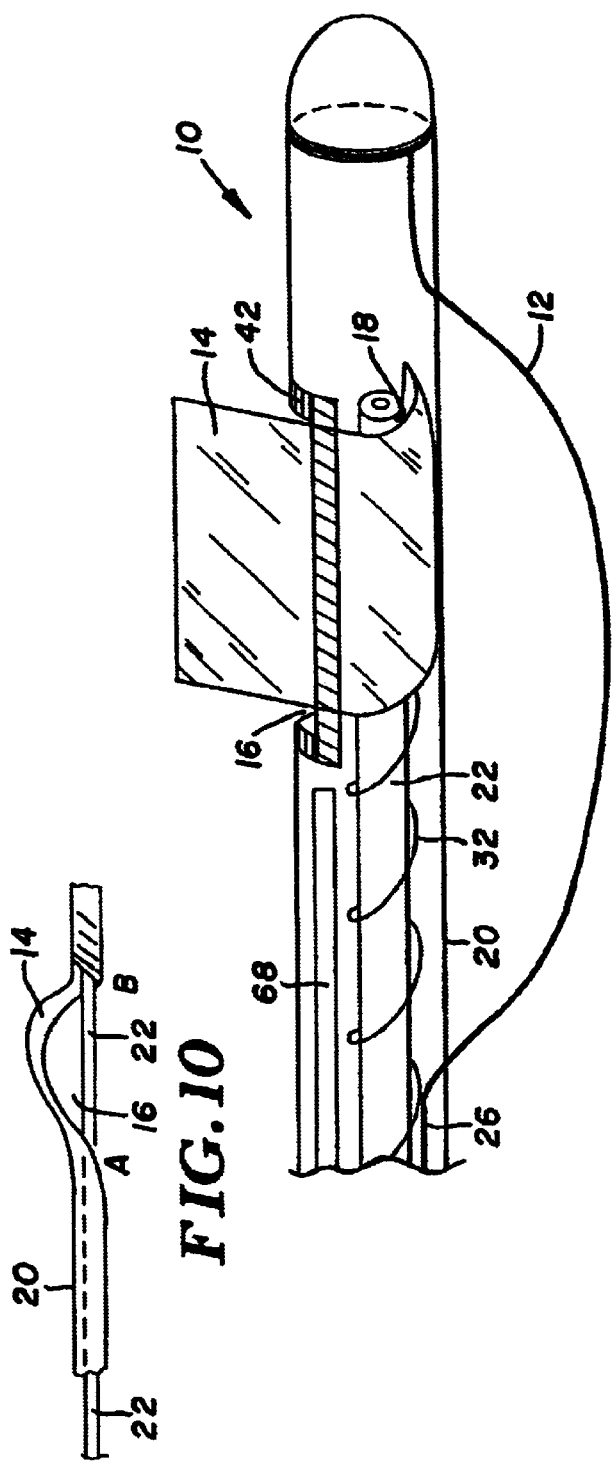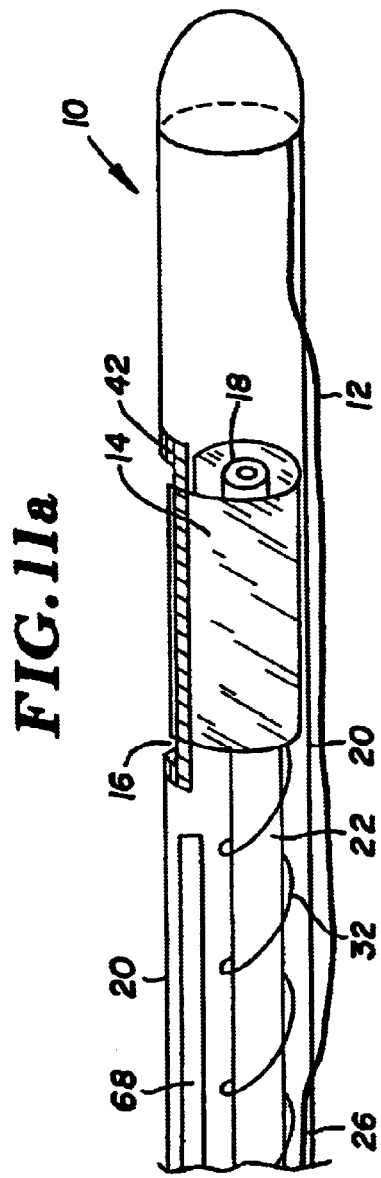

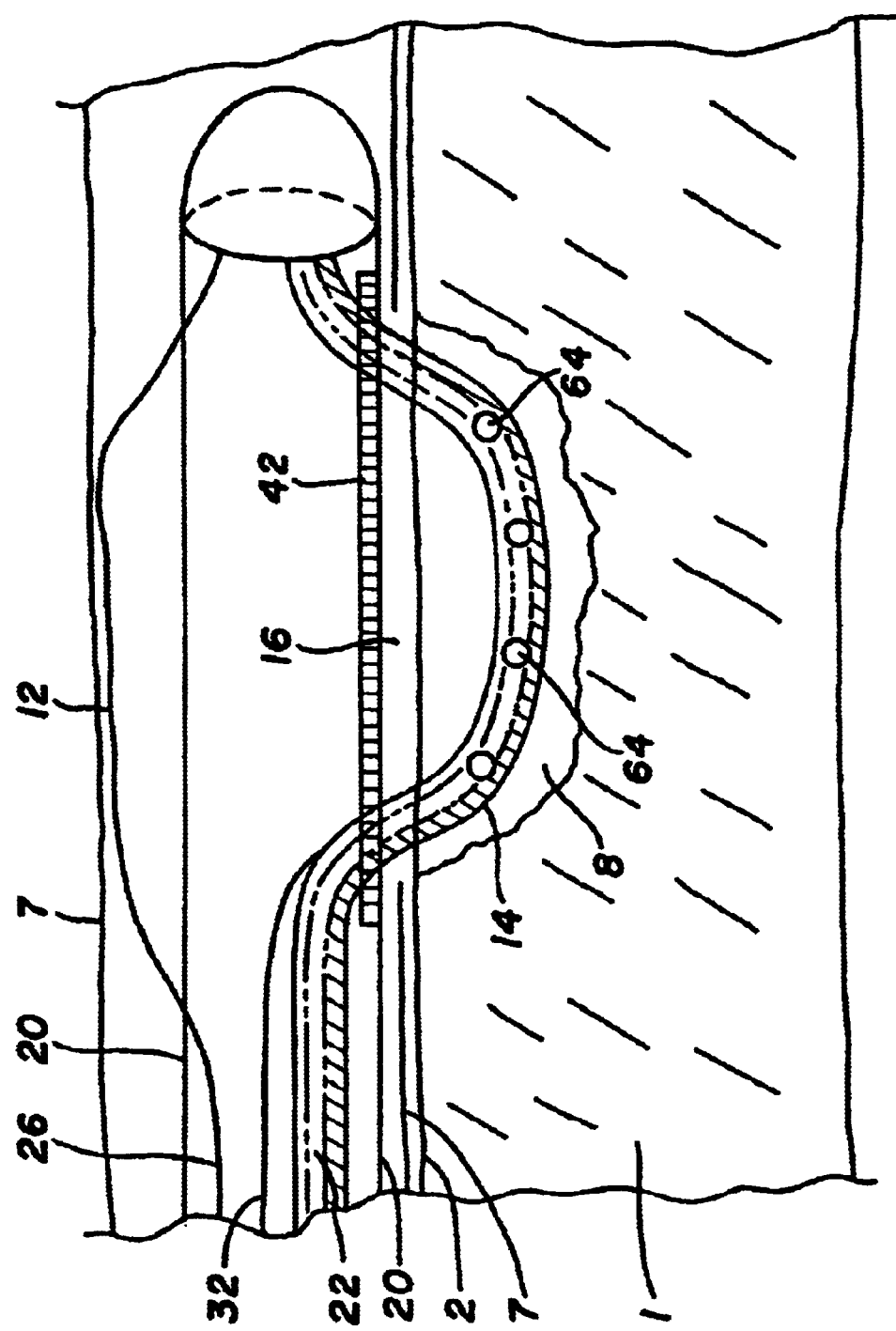

PERCUTANEOUS TRANSMYOCARDIAL REVASCULARIZATION (PTMR) SYSTEM

This application claims the benefit of priority based on Provisional Application No. 60/147,687 entitled "Percutaneous Transmyocardial Revascularization (PTMR) System," filed Aug. 6, 1999.

This application is a continuation-in-part of U.S. patent application Ser. No. 09/256,020 (now U.S. Pat. No. 6,214,024), filed Feb. 23, 1999 as a divisional of U.S. patent application Ser. No. 08/899,490 (now U.S. Pat. No. 5,876,369), filed Jul. 19, 1997 as a divisional of U.S. application Ser. No. 08/376,226 (now U.S. Pat. No. 5,665,062), filed Jan. 23, 1995.

BACKGROUND OF THE INVENTION

Creating channels in ischemnic myocardial tissue has been demonstrated to elicit an angiogenic response in the affected tissue. Revascularization has been associated with a decline the angina symptoms of patients suffering from severe diffuse coronary artery disease, especially that which is refractory to standard therapeutic modalities (Agarwal R, et al. Transmyocardial laser revascularization: early results and 1-year follow-up. *Ann Thorac Surg.* 1999;67(2):432–6). Clinical studies for transmyocardial revascularization have primarily involved direct access to the epicardium of the heart, which facilitates creating the desired grid of small diameter channels throughout the surface of the heart, but increases the morbidity and mortality of the procedure.

Experimental studies demonstrate an increase in perfusion for the treated tissue. Malekan, et al studied the pathophysiology of discrete bores or channels generally normal to the endocardial surface created with a $CO_2$ laser and a power drill (Malekan R, et al. Angiogenesis in transmyocardial laser revascularization. A nonspecific response to injury. *Circulation.* 1998;98:II62–5). The average channel diameter was less than 1 mm for both the $CO_2$ laser and the power drill (Malekan, et al). Newly created microvessels at high density were detected immediately within the channels, while the creation of new vessels dropped to a negligible amount at distances greater than 5 mm from the channel center (Malekan, et al). Such studies demonstrate that several discrete channels narrowly dispersed (e.g. separated by less than approximately 5 mm) throughout the chamber of the heart are needed to maximize revascularization. Therefore, to transform surgical transmyocardial revascularization into a viable catheter-based approach, the creation of channels must be optimized through remote manipulation of the cutting mechanism.

Conventional catheter-based approaches for myocardial revascularization use laser, radiofrequency, and drilling to create several discrete, small diameter bores into the myocardium. These approaches require manipulating the distal tip of the catheter to position the cutting mechanism against the endocardium, then forming bores through the endocardial surface and into the myocardium. Manipulation of a catheter within the ventricle is burdened by the trabeculated surface of the ventricles and the prominence of anatomic structures such as the papillary muscles. The ventricular anatomy therefore hinders the ability to reliably position the distal tip of a catheter at numerous unique locations along the endocardial surface. Hence, current catheter-based transmyocardial revascularization approaches do not produce an optimal dispersion of channels or bores required to maximize the therapeutic response.

Prior approaches for transmyocardial revascularization involve positioning the distal tip of a cutting element against the endocardial surface (or epicardial surface) and creating a small diameter (<1 mm) channel or bore 4 extending into the myocardium, as shown in FIG. 1b.

As seen from FIG. 1a, which like FIG. 1b is a cut-away view that shows a thickness 9 of the myocardium, channels 4 are perpendicular to endocardial surface 2, and extend lengthwise in to the myocardial thickness. Viewed along the endocardial surface, bores 4 appear circular, and are depicted as dots in the figure. Cutting elements for prior approaches have included fiberoptics focusing laser energy into adjacent tissue, mechanical drill bits designed to bore through the myocardium, and small diameter (needle) electrodes designed to coagulate tissue while being advanced into the myocardium. As shown in FIG. 1a, prior percutaneous transmyocardial revascularization (PTMR) approaches require creating numerous channels 4 throughout the endocardial surface 2 of the heart. To produce the desired angiogenic response with prior approaches, several discrete channels 4 must be created along the endocardial surface. To maximize the angiogenic response using prior approaches, the channels need to be separated by less than about 5 mm. This maximizes the formation of new vessels throughout tissue located between discrete channels. Surgical approaches for transmyocardial revascularization can produce the desired dispersion of channels since the operator has direct access to the endocardial surface. However, it is difficult to remotely operate a catheter during percutaneous transmyocardial revascularization to accurately position the catheter to create a suitable dispersion of channels to maximize the angiogenic response.

To position prior PTMR catheters 5, physicians use preshaped introducing sheaths to direct the distal tip of a PTMR catheter 5 against the endocardial surface 2. Such introducing sheaths 6 have preformed curves configured to orient the distal tip of a prior PTMR catheter 5 against the endocardium, sufficient rigidity to stabilize the catheter against the endocardium while creating the bore, and substantial torque response to facilitate repositioning the catheter at numerous endocardial locations. Alternatively, prior PTMR catheters incorporate steering mechanisms (unidirectional or bidirectional) to help deflect the distal tip of the PTMR catheter towards the endocardial surface. Even with the aid of introducing sheaths or steering mechanisms to help position prior PTMR catheters, deficiencies associated with reliably creating a grid of channels through the endocardial surface limit the utility and effectiveness of prior PTMR catheters.

The right and left ventricles of the heart are highly trabeculated and incorporate anatomic structures, such as the papillary muscles 3, that direct the distal tips of prior PTMR catheters 5 to a limited number of unique positions. Even with introducing sheaths 6 or steering mechanisms to aid positioning prior PTMR catheters 5, the distal tips of these devices still migrate toward few unique locations while being manipulated inside the heart. The distal tips of prior PTMR catheters migrate between the trabecula of the heart and towards the base of the papillary muscles, even when a portion of the heart is infarcted. The best analogy to the problem of current methods of PTMR is cardiac ablation for ventricular tachycardia. Numerous preclinical and clinical studies involving the creation of thermally induced lesions along the endocardial surface have been performed. Common observations arose for the studies—the distal tips of steerable and preshaped catheters migrate toward six to twelve unique positions. This prevents the required distribution of channels throughout the endocardial surface to optimize the myocardial revascularization response, especially when considering that surgical transmyocardial revascularization procedures are performed with an average of twenty three discrete channels to realize the desired therapeutic response (Agarwal, et al). The inability to reliably distribute the channels throughout the endocardial surface significantly reduces the angiogenic response and accompanying therapeutic effects of the procedure.

Even attempts to incorporate guide members to more accurately position the distal cutting tip of the catheter do not effectively address the deficiencies of positioning a small diameter channel creating device at numerous positions throughout the endocardial surface of the heart. These prior devices still create channels having a circular profile or a cross-section in which the length is approximately equal to the width and a depth that is substantially greater than the diameter (or length and width). For example, U.S. Pat. No. 5,910,150 entitled "Apparatus for Performing Surgery" by Saadat describes a guide mechanism in which an end-effector (distal cutting tip) is able to move. The guide enables repositioning the end-effector at discrete locations throughout the endocardial surface, depending on the amount of advancing or retracting of the end-effector. Once positioned, this tubular end-effector must be advanced from the guide mechanism and extend into the myocardium a depth that is larger than the diameter of the end-effector. Control of the end-effector emanating from the guide mechanism decreases, the more the end-effector is extended away from the guide mechanism. In addition, numerous steps of advancing (or retracting) the end-effector, deploying the end-effector to create a discrete channel, withdrawing the end-effector, and repositioning the end-effector must be performed to create a distribution of channels capable of inducing an angiogenic response. In addition, the dispersion of channels depends on how far the operator repositions the end-effector between small diameter bores, producing inconsistencies in the distance between bores that may impact the complete angiogenic response.

When advancing prior PTMR catheters through valve structures, they are typically advanced through an introducing sheath previously inserted through the valve. Alternatively, prior PTMR catheters are steered, or otherwise manipulated into a pigtail, within the aorta, before insertion through the valve. This complicates the deployment of prior PTMR catheters into the desired heart chamber.

SUMMARY OF THE INVENTION

Percutaneous transmyocardial revascularization devices according to the present invention disclosed herein enable a physician to quickly create thin, linear channels or incisions through the endocardial surface and into the myocardium, to elicit an angiogenic response. New vessel growth is promoted by the healing process, and may be enhanced by the application of an angiogenic substance. In addition, the devices enable the physician to more reliably distribute the channels throughout the heart to optimize the physiologic response of the transmyocardial revascularization.

The invention relates to devices that more quickly and efficiently produce transmyocardial revascularization during catheterization procedures. More particularly, the invention relates to catheters that create thin, linear incisions through the endocardium and into the myocardium. The devices more rapidly and consistently produce channels capable of maximizing the therapeutic effects of the associated angiogenesis. The catheters of the invention address the deficiencies of conventional catheter-based methods that create random, discrete, small diameter channels or bores (<1 mm) into the myocardium. Each of the thin, linear incisions created according to this invention produces the same result as several bores created with conventional approaches. As a result, the catheters of this invention more reliably treat the entire surface of the heart to elicit the desired physiologic response, with considerably reduced need for repositioning the catheter.

The catheters of the invention do not require positioning their distal tips against the endocardium when producing channels through the endocardial surface and into the myocardium. Instead, these catheters are positioned lengthwise against the endocardial surface. In contrast to prior approaches, the distal tip of this catheter is non-functional and atraumatic. Use of this catheter produces a reduced number of thin, linear incisions. Thus, fewer catheter placements effect a comparable angiogenic response comparable to several small diameter channels narrowly dispersed throughout the endocardial surface. This approach also enables a more accurate placement of the channels throughout the endocardial surface to ensure revascularization of the entire targeted region, as opposed to randomly creating channels at locations within the heart chamber where the distal tip of a conventional catheter tends to migrate.

The catheters of the invention also enable injecting therapeutic solutions (e.g. drugs or genetic compounds) into cut tissue for localized delivery of therapeutic solutions. The catheters also provide the ability to actively stimulate tissue to facilitate intracellular application of the therapeutic solutions. For example, the cutting element may function as an electrode to deliver high voltage electrical pulses into cut tissue to cause electroporation of tissue within the cut region.

IN THE DRAWINGS

Figure 3A:
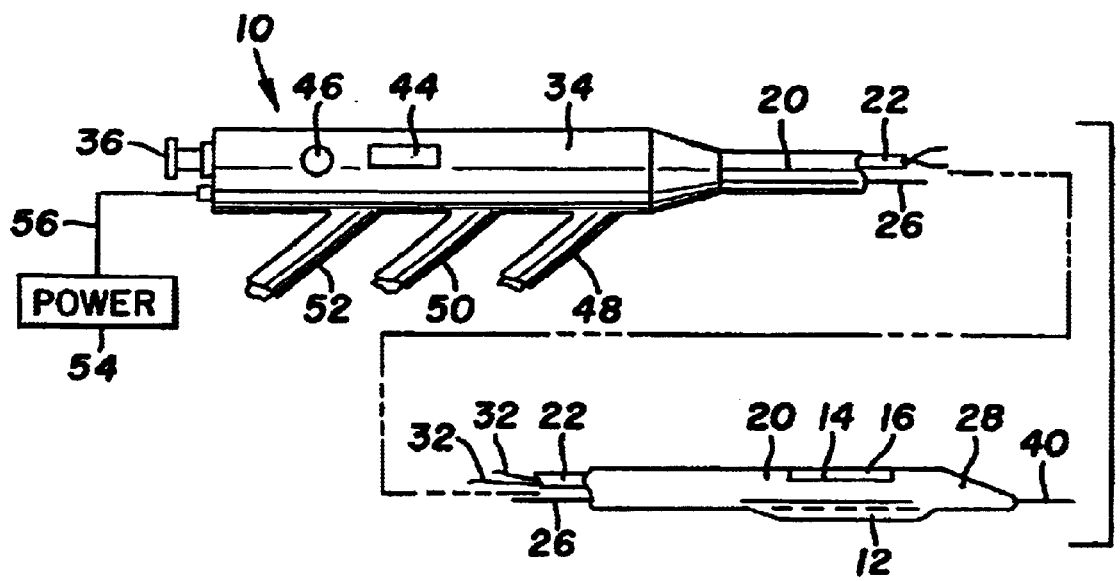
FIG. 3a is a side elevation of the percutaneous transmyocardial revascularization catheter.
Figure 3B:
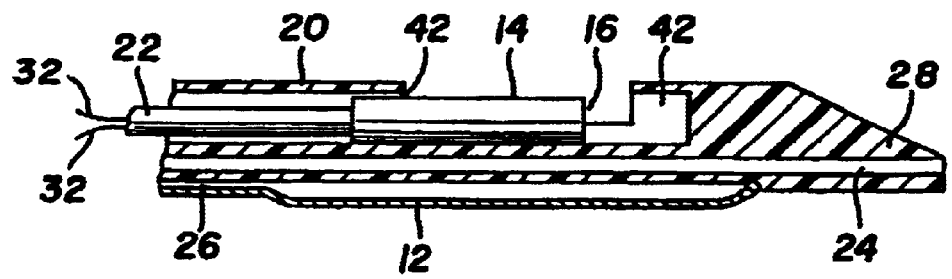
Figure 4A:
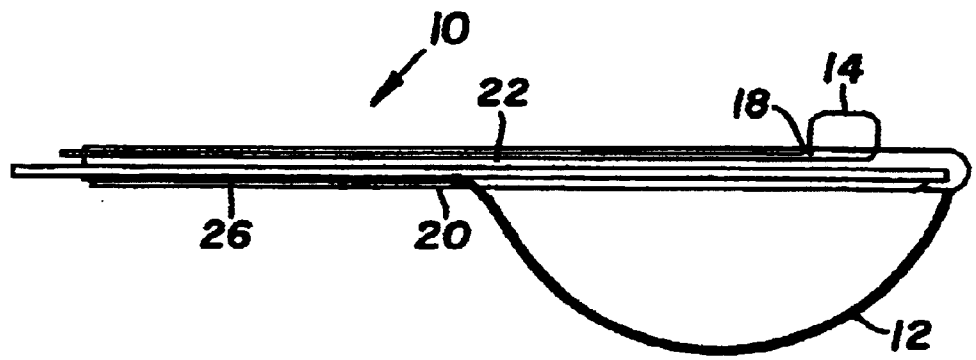
Figure 4B:
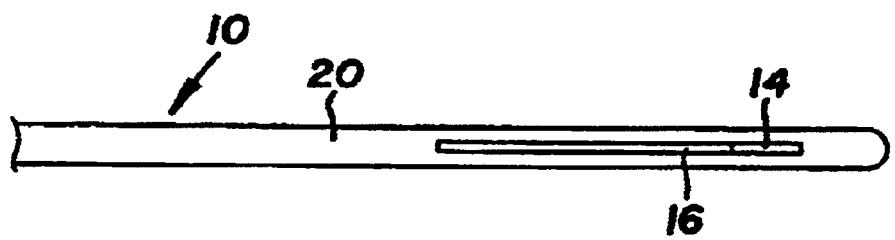
Figure 4C:
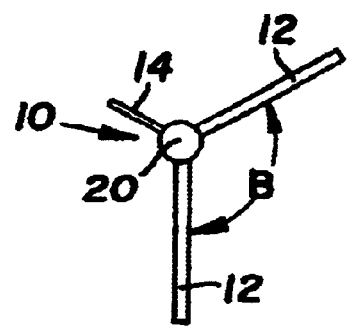
Figure 13:
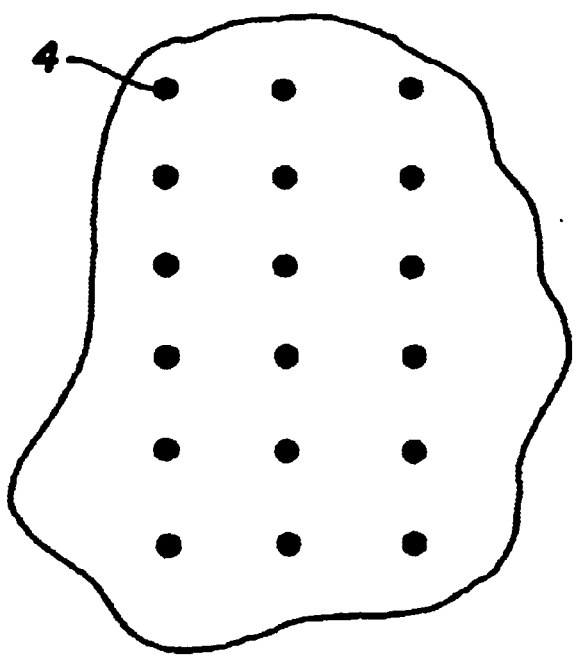
Figure 14:
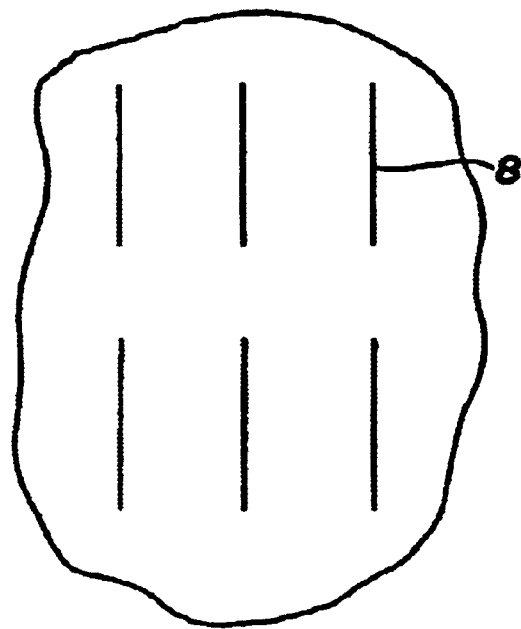

FIGS. 3b–f are enlarged views of the distal end of the catheter in FIG. 3a;

FIGS. 4a–c show the distal end of the catheter of the invention;

FIG. 5 shows an alternative catheter of the invention that incorporates an atraumatic distal end;

FIGS. 6a–e show alternative embodiments of the invention capable of creating several thin, linear incisions simultaneously;

FIGS. 7a–e show representative cutting elements for creating the thin, linear incisions;

FIGS. 8a–b are side views of the cutting mechanism for creating thin, linear incisions of the invention;

FIGS. 9a–e are side views of representative cutting elements for creating thin, linear incisions;

FIG. 10 is a side view of an alternative embodiment of a cutting element of the invention;

FIGS. 11a and b are side views of an alternative catheter embodiment;

FIG. 12 is a side-sectional view of a catheter of the invention used to create thin, linear incisions initiating in a coronary artery and extending into the myocardium; and FIGS. 13 and 14 respectively illustrate a region of myocardial tissue treated with a conventional catheter, and treated with a catheter according to the present invention, respectively.

DETAILED DESCRIPTION OF PREFERRED EMBODIMENTS

The catheter systems are intended to create thin, linear channels capable to treating cardiac abnormalities such as angina, cardiovascular disease, ventricular tachycardia, atrial fibrillation, ventricular fibrillation or other applications benefiting from revascularization or ablation. The devices of the invention are applicable to surgical and well as percutaneous approaches to inducing angiogenesis in cardiac or other tissue.

To overcome the deficiencies of the prior art, catheters of the invention do not position a distal cutting tip against the endocardium when producing channels through the endocardial surface and into the myocardium. Instead, the catheters 10 of the invention are designed for a "sideways" placement, to position a length of the catheter against the endocardial surface and ensure intimate tissue contact with the side of the catheter through the use of support strands 12. In contrast to prior approaches, the distal tip of this catheter is non-functional and includes an atraumatic structure to prevent perforating the ventricle, tearing the valves, or abrading the endocardium. The approach described by this invention produces a number of thin, linear channels 8 (having a length substantially greater than the width), with few catheter placements, capable of effecting the same or superior angiogenic response as several, closely spaced, small diameter channels dispersed throughout the endocardial surface. The thin, linear channels created with the catheter(s) of the invention have a length that is at least twice the width. This approach also enables accurate placement of the channels throughout the endocardial surface to ensure revascularization of the entire targeted region, as opposed to randomly creating channels wherever the distal cutting tip of the catheter migrates (even if guide mechanisms are utilized to position the distal cutting tip), characteristic of prior approaches. The present applications involve devices previously disclosed in U.S. Pat. No. 5,665,062 entitled "Atherectomy Catheter and RF Cutting Method" filed Jan. 23, 1995, U.S. Pat. 5,876,369 entitled "Tissue Removing Catheter and RF Cutting Method", and pending U.S. patent application Ser. No. 09/256,020 entitled "Tissue Cutting Catheter and RF Cutting Method" to percutaneous transmyocardial revascularization procedures involving cutting and coagulating tissue along the catheter axis. Embodiments of the invention can utilize cauterization of tissue to produce the desired channels or mechanical incising of the endocardial surface with a sharp cutting element(s). The catheters of the invention also address the distribution of channels along the catheter axis with sections of intact endocardium between distinct channels to preserve the structural integrity of the heart wall, prevent aneurysm formation, and still elicit the desired revascularization response.

Figure 2A:
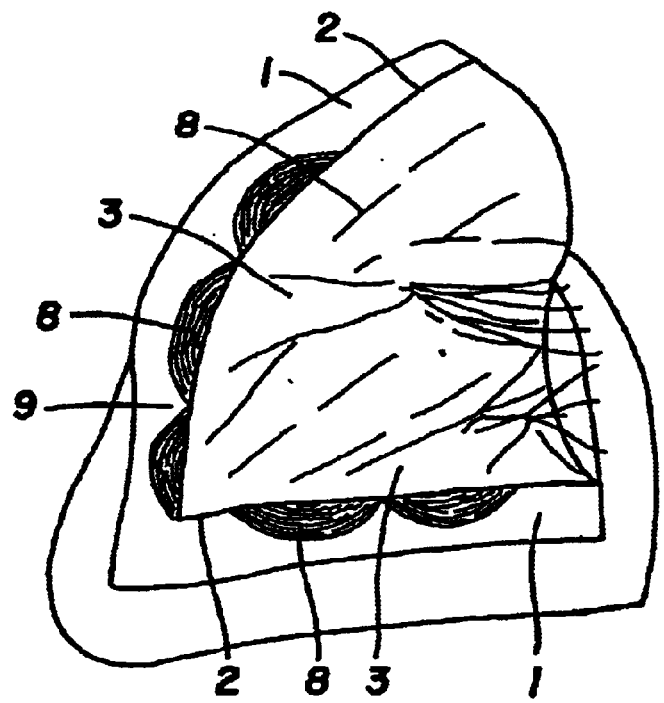
FIG. 2a shows a heart wall containing thin, linear channels created according to the invention.

Referring more particularly to the drawings, FIG. 2a illustrates a heart in which a number of thin, elongate linear channels or incision 8 have been created throughout the endocardial surface 2 with the catheter of the invention 10. The channels created with the embodiments of the invention have lengths exceeding their widths and depths. As best seen in the cut-away views of myocardial thickness 9, incisions 8 have rounded or crescent-like profiles, with the length of each incision running along endocardial surface 2, and a depth extending in the myocardial thickness direction. Further, when one views the endocardial surface, incisions 8 appear as thin lines. The length of each line corresponds to the incision length. The width of each line corresponds to a thickness dimension of the incision, which typically is substantially the same as the cutting element thickness, e.g., 1 mm or less. Thus, channels formed according to the invention are referred to as thin, elongate and linear, in contrast to the typically circular bores that extend into the myocardium in its thickness direction. As previously stated the thin, linear channels preferably have lengths that are at least twice as large as the widths and lengths that are greater than the depths. The thin, linear channels may in fact have lengths as much as ten or twenty times the width and still elicit the desired angiogenic response and maintain the structural integrity of the heart (e.g. not impact wall motion). The thin, linear elongate channels created with the catheters of the invention also enable minimizing the depth and increasing the length to maintain the desired angiogenesis. The healing response has been demonstrated to occur a short distance beyond cut tissue. This is why conventional techniques are able to obtain the desired angiogenesis with small, diameter channels dispersed approximately less than 5 mm apart. The present thin, linear elongate channels having a limited depth are able to elicit the desired angiogenic response and better ensure structure integrity of the myocardium. It should be noted that although the thin, linear channels are depicted as extending along a line, the section of the catheter incorporating the windows may be fabricated as an arc, circle, or alternative geometry to produce thin, linear channels having a curved or other desired shape. In other words, the lines representing incisions 8 in FIG. 2a would be curved rather than straight.

Figure 2B:
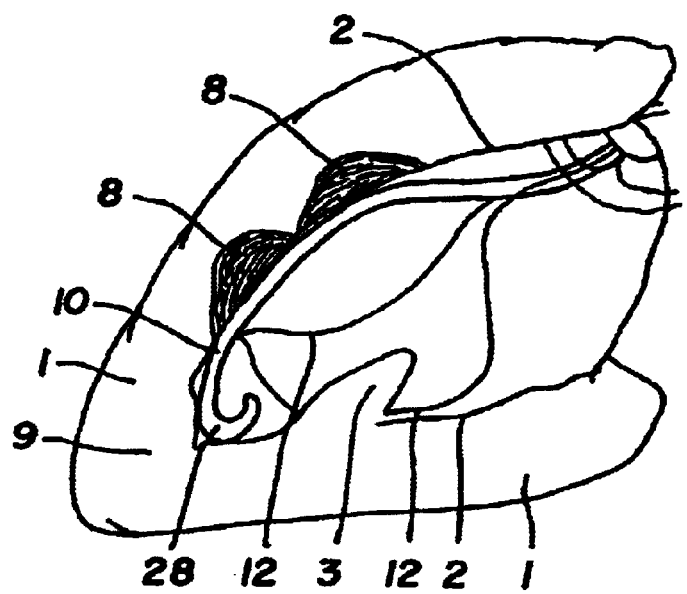
FIG. 2b illustrates the operation of a catheter of the invention.

As shown in FIG. 2b, the catheter is introduced through the aortic valve during retrograde access into the left ventricle, through the mitral valve; during transeptal access from the right atrium to the left atrium, past the interatrial septum, and into the left ventricle; or through the tricuspid valve to access the right ventricle. A pigtail 28, formed at the distal end of the catheter or other such atraumatic structure, facilitates inserting the catheter 10 through the valves without perforating or otherwise damaging the valve structures. FIG. 5 shows another atraumatic structure for advancing the catheter through the valves. In this configuration, the distal tip is formed as a corkscrew having either less than a single turn or multiple turns. This configuration also helps stabilize the catheter into the trabecula of the heart or at the apex to provide an anchor with which to support the catheter. In addition to the atraumatic distal tip, the catheter of the invention may incorporate a lumen to pass a guidewire 40 (as shown in FIGS. 3a and b) from a port 50 at the handle through a lumen connecting the port to the distal tip of the catheter. The guidewire aids in advancing the catheter through the vasculature and past the valves. This port 50 (or another port, 48 or 52) may also be used to inject contrast fluid to be used when performing angiography for evaluating wall motion or other diagnostic parameters of the heart. A pressure monitoring device could also be inserted into the lumen, or a port (48 or 52) may be attached to a pressure transducer; other diagnostic tool may be used in conjunction with the lumen and port.

Once positioned inside the right or left ventricle, the atraumatic distal tip of the catheter is positioned at the apex of the ventricle. Then, the support strands 12 are manipulated (e.g. advanced) into contact against the endocardial surface of the heart to urge the side of the catheter containing the window and the cutting element against the endocardial surface, as shown in FIG. 2b. The support strands 12 are formed of plastic, metal (e.g. titanium), alloy (e.g. stainless steel or nickel titanium), or combination, wire, wire coil, hypotube, rod, band, combination of the aforementioned, or other geometry. As shown in FIGS. 4a and c, the support strands 12 are attached to a stylet 26 designed to manipulate the support strands within the heart chamber. The stylet 26 extends through the catheter body to at least one actuator knob 44 shown in FIG. 3a, or sliding mechanism. A deployment indicator 46 may signal the extension of the support strands 12 away from the catheter body. When the support strands are fully deployed, sudden rotation of the catheter may abrade tissue contacting the support strands. Therefore an indicator displaying the position of the support strands aids the operator in identifying the orientation of the support strands relative to the catheter body. The indicator may simply be a reference marking on the actuator knob or sliding mechanism that is visible to the operator once it is positioned through a window incorporated in the handle after the knob is fully retracted. The visible indicator signals that the support strands are fully retracted into the catheter body and the operator can safely withdraw the catheter into the vasculature or rotate the catheter to a new position within the heart.

Preferably two support strands 12 are used to urge the catheter body 20 against the endocardial surface. More than two support strands may be used. While one support strand may even be used, two support strands separated by an angle B, shown in FIG. 4c, provide the desired support of the catheter body against the endocardial surface. A single stylet may be used to actuate multiple strands. Preferably, separate stylets are attached to separate support strands 12 to better ensure stability of the catheter within the heart chamber and enable extending individual support strands at different lengths to maximize the contact between the catheter and the endocardial surface. The ability to independently actuate the support strands is especially important when the distance between the catheter axis and the endocardial surface varies for each distinct support strand 12. A locking mechanism on the handle may be used to hold the support strands 12 in their deployed position. The actuator knob 44 or sliding mechanism may incorporate a screw mechanism, which the operator may tighten and produce a friction fit against the handle therefore locking the support strands in place. The distal ends of the support strands are secured to the distal end of the catheter using adhesives, crimping, ultrasonic welding, soldering, or other bonding process. A collar may be used to reinforce the bond at the distal end of the catheter. The cross-sectional geometry of the support strands may be chosen to tailor the stiffness to the application. For stiffer support strands, wider and/or thicker cross-sections may be used. The stiffness may be tapered from the distal end proximally or from the middle of the deployed support strand proximally and distally to better conform the support strands to the endocardial surface.

The catheter wall defines a compartment bordered by the interior surface of the catheter tubing. As shown in FIGS. 3a to f, and FIGS. 4a to c, at least one window 16 defining an opening through the catheter wall is incorporated longitudinally along the catheter wall opposite the sides of the catheter from which the support strands 12 emanate. The number of windows depends on the number of separate axial channels required to elicit the desired angiogenic response without adversely affecting the integrity of the heart chamber. The at least one window 16 is positioned against the endocardial surface once the support strands are actuated. A cutting element 14 is movable along the catheter axis by remote actuation of a stylet 22 which is connected to the cutting element 14 at the distal end of the catheter and is attached to a knob 36 or sliding mechanism at the proximal handle 34. As the cutting element 14 enters the region defined by the at least one window 16, the cutting element extends radially outward from the catheter and contacts tissue adjacent the at least one window 16.

The number of windows 16 and length of each window can vary depending on the desired channel distribution characteristics. When numerous, short channels are desired, the length of each window is minimized and the separation between discrete windows is chosen to tailor the distance between channels. For example, to emulate the size and distribution of surgical transmyocardial revascularization channels, the length of the windows may be kept below 2 mm (also requiring a cutting element with a relatively short width in its deployed configuration) and the spacing between windows may be specified at approximately 5 mm. Longer windows are fabricated when fewer, longer channels are desired. Channels substantially longer than 1 mm, which are thin (width less than 1 mm), have the capacity to not only increase the density of new vessels formed within the channel but also increase the density of new vessels produced in the area distant (approximately 5 mm) from the channels.

A stylet or drive rod 22 is used to manipulate the cutting element. The drive rod 22 is formed of a wire coil, hypotube, or rod which is coated with, wrapped by, or inserted through a tubing of an electrically insulative material (e.g. PTFE, PET, or polyimide). The drive rod exhibits a high degree of axial flexibility to permit bending as the catheter is deflected within the anatomy but has significant column strength to permit advancing, rotating, and/or retracting the cutting element within the catheter. As the cutting element is moved along the catheter by manipulation of drive rod 22, the cutting element is advanced, rotated, or retracted from inside a constraining means defined by the compartment to an open area defined by window 16. As shown in FIGS. 3d, and 4a, the cutting element 14 extends radially beyond the external surface of the catheter when the cutting element is manipulated beyond the confines of the compartment and is positioned within an open area defined by the window. This causes the cutting element to extend beyond the outer diameter of the catheter wall thereby contacting tissue adjacent the window. Then, the cutting element is used to incise the endocardial surface and a depth of myocardium as it is moved axially (longitudinally) relative to the catheter. This produces the thin, linear channels 8 through the endocardial surface along the length of catheter defined by window 16. As the cutting element is advanced, rotated, or retracted past the window, the compartment compresses the cutting element into a low profile such that it is enclosed within catheter wall 20 and isolated from tissue by the wall.

The at least one window may be reinforced with a support structure 42 fabricated from a metal (e.g. titanium or platinum), alloy (e.g. platinum iridium, stainless steel or nickel titanium), thermoplastic, thermoset plastic, or combination of the aforementioned materials into a composite structure; other materials may also be used. The ends of the window support structure(s) 42 must have sufficient rigidity to compress the cutting element into a reduced diameter as the cutting element is advanced or retracted past the window opening. This is especially important when the edge of the cutting element is sharp and the ends of the window must resist splitting or abrading as the cutting element is compressed. The sides of the window support structure(s) 42 must have sufficient rigidity to compress the cutting element into a reduced diameter as the cutting element is rolled past the window opening. In addition, the sides of the window support structure(s) must have sufficient flexibility to follow the contours of the catheter as it is positioned into contact with the endocardial surface. This helps ensure consistent contact between the side of the catheter and the tissue surface.

The cutting elements shown in FIGS. 8a and b and FIGS. 9a to e are preshaped members formed into a desired geometry. One representative fabrication process for the preshaped cutting elements involves forming the raw material into a desired geometry, exposing the material to sufficient heat to anneal the material into this predetermined shape, and allowing the material to cool in the preformed shape by quenching or other process. This process applies to metals, alloys, (e.g. nickel titanium) and polymers. The preshaped cutting elements are compressed into a low profile by advancing or retracting the cutting element into the confines of the catheter wall. Once the cutting element is positioned within the area defined by the window, the force causing the cutting element to compress into a low profile is removed, causing the cutting element to return towards its pre-formed shape thereby extending radially beyond the outer diameter of the catheter and into contact with adjacent tissue.

As to geometry, the cutting element may be formed with a radial segment extending at an angle between 30 and 150 degrees from the axis of the catheter, as shown in FIG. 8a. The cutting element may alternatively be formed with a coiled segment extending between just less than one turn to greater than one turn, as shown in FIG. 8b. Alternative embodiments for the cutting element are shown in FIGS. 9a to d. The cutting element may be fabricated as a triangle having a distal angle A between 15 and 135 degrees. Alternatively, the cutting element may be formed with a curved segment or a trapezoidal segment extending from the axis of the drive rod 22 a height H designed to tailor the depth at which the cutting element extends into the myocardium, as shown in FIGS. 9c and d. The cutting elements described previously straighten as they are compressed within the catheter body, as shown in FIG. 9a.

FIG. 10 shows a different expansion mechanism associated with the cutting element. Instead of depending on the memory elastic properties of the cutting element to force the cutting element into contact with tissue in the vicinity of the at least one window, the cutting element is manually deployed. In this embodiment, the distal end of the cutting element 14 is attached to the drive rod 22 and the proximal end is attached to the catheter tubing 20 or to a tubing (not shown) covering the drive rod 22. Using a separate tubing from the catheter body 20 as the anchor for the cutting element permits axial movement of entire cutting element relative to the catheter body. Therefore, one cutting element may be used for various locations along the catheter axis. As the drive rod 22 is retracted, the cutting element 14 is urged against the tissue surface. As the drive rod 22 is advanced, the cutting element 14 is straightened into a reduced diameter for atraumatic movement through the vasculature or repositioning at another endocardial location.

The cutting element may be configured to mechanically cut the endocardium and a depth of the myocardium, depending on the geometry of the cutting element. The cross-section of the mechanical cutting element is fashioned with sharp edges, as shown in FIGS. 7a to c. The entire surface of the cutting element may be fabricated with sharp edges. Alternatively, as shown in FIG. 5, one of the proximal 60 and distal edges 58 may be fabricated with a sharp edge while the top edge 62 (if any) and the other of the proximal and distal edges are fabricated relatively blunt. The later configuration enables more controlled cutting of tissue by exposing the sharp edge of the cutting element to tissue only as the cutting element is moved in one direction (e.g. advanced or retracted). When the cutting element is moved in the other direction, the cutting element does not damage the tissue surface. This enables cutting the desired channels at one location, reloading the catheter to reposition along another line of tissue and cutting additional channels. Alternatively, the mechanical cutting element may be configured with a sharp angle A, as shown in FIG. 9b, such that the tip of the mechanical cutting element is sharp so it is able to cut a depth of tissue when the cutting element is manipulated within the at least one window causing the cutting element to deploy into contact with adjacent tissue.

The cutting element may alternatively be configured with at least one electrode that cauterizes or simultaneously cuts and coagulates tissue by transmitting radiofrequency energy or direct current energy to the at least one electrode. By delivering radiofrequency energy or direct current energy to the at least one electrode attached to the cutting element, tissue contacting the electrode(s) heats and movement of the cutting element along the heated tissue incises adjacent tissue while simultaneously coagulates the cut tissue. When adapting the catheter to transmit radiofrequency energy to the electrode, a first signal wire is connected to the electrode and is routed to one lead of the radiofrequency generator; a second signal wire is connected to a remote indifferent patch electrode placed on the patients body and having a large surface area to prevent skin burns or to a second electrode placed on the cutting element, on the catheter distant from the electrode, or on a separate cutting element and is routed to the second lead of the generator. When adapting the catheter to transmit direct current energy to the electrode, the electrode is fabricated from a higher resistive material and has the two signal wires attached to the electrode at separate ends of the electrode and routed to separate leads of a power generator.

The electrode may be fabricated from stainless steel, nickel titanium, platinum, platinum iridium, gold, titanium, tungsten, tantalum, or other material. The cutting element may be fabricated from a conductive material (listed above) and shaped to function as the cutting element and the electrode. The cutting tool/electrode can be single or multiple, formed from a wire, flattened wire, tube, band, coil, flat sheet, a combination of these components, or other desired form. The resulting shape can be round, rectangular, oval, coiled, angled, flat, or any desired combination of these shapes. Alternatively, the electrode may be attached to the cutting element as a separate component aside from the cutting element support structure. For example, a cutting element fabricated from a thermoplastic material or thermoset plastic may incorporate a small diameter wire attached around the periphery of the cutting element, as shown in FIG. 4a. This decreases the surface area of the electrode producing higher current densities emanating from the electrode, and resulting in more efficient and localized heating of adjacent tissue. In addition, this cutting element embodiment minimizes the formation of coagulum on the cutting element; coagulum can reduce the current density near the electrode and adversely impact the cutting efficiency of the cutting element. Alternatively, the electrode may be deposited (e.g. ion beam assisted deposition, sputter coating, pad printing, silk screening, soldering, vacuum deposition, painting conductive epoxy, or other method) on a non-conductive cutting element, or the deposition may be used to increase the conductivity of a conductive cutting element. Deposited electrodes are flexible and follow the contours of the cutting element.

The cutting element containing at least one electrode may alternatively be fabricated by extruding, injection molding, or otherwise applying a nonconductive, conformal coating (e.g. elastomer) over a conductive cutting element 14. In a second operation, the outside surfaces of the cutting element coating are removed exposing the electrodes. The cutting element is preshaped so the outside surface defining the at least one electrode contacts tissue adjacent the window 16, once positioned. As described with the mechanical cutting element embodiment, the electrode may be positioned on the distal edge 58, proximal edge 60, or top edge 62 (if any) of the cutting element FIG. 9e shows a cutting element 14 configured with a curved geometry and having the electrode on outside edge of the cutting element. The cross-section of the electrode may be fabricated with sharp edges as shown in FIGS. 7a to c or relatively blunt edges as shown in FIGS. 7d and e.

Signal wires 32 may be connected to the electrodes through spot welding, mechanical fit, or soldering, and are routed to the leads of a radiofrequency generator 54. The signal wire may be fabricated from copper, platinum, stainless steel, or a composite of materials (e.g. platinum and silver combined by a drawn filled tubing process). The composite signal wire uses the silver as the inner core to better transit radiofrequency energy or direct current energy. The signal wires may be fabricated with a circular, elliptical, rectangular (flat), or other geometry depending on the design of the electrode and space available in the catheter. The signal wires are jacketed with an insulative layer such as polyimide, polyamide, polyurethane, polyester, or other material. The drive rod used to manipulate the cutting element may alternatively be fabricated from a conductive material and serve as a signal wire for transmitting radiofrequency energy or direct current energy to the electrode. In this case, the knob used to manipulate the drive rod would be fabricated from an insulative material; in addition, the drive rod would be covered with an insulative layer.

The electrodes may be coated with materials such as silicone fluid or hydrophilic coatings that are biologically inert and reduce the surface friction. Alternatively, the electrodes and other catheter structures may be coated with heparin, or thrombolytic substances designed to prevent thrombosis or coagulum adherence.

FIGS. 6a to e show alternative embodiments that demonstrate additional characteristics for the catheter of the invention. As shown in FIG. 6a, multiple cutting elements 14 are shown with multiple windows 16. The cutting elements 14 are secured to a single drive rod 22; alternatively, the cutting elements may be attached to independently movable drive rods. These cutting elements, as previously described, are adapted to compress into a reduced diameter to isolate the cutting elements from the tissue and extend radially outward when the cutting elements are advanced or retracted into the region defined by the windows 16. The use of multiple cutting elements 14 decreases the time required to create the desired channels. FIGS. 6d and e show another enhancement where multiple cutting elements are separated by an angle A1 between the cutting elements 14. The windows created in the catheter wall are also separated by the angle A1 to expose the cutting elements as the cutting elements are advanced or retracted into the regions defined by the windows.

An alternative embodiment for the catheter of the invention uses rotation of the drive rod 22 to deploy the cutting element into an expanded orientation where the cutting element contacts tissue and compress the cutting element into a reduced diameter isolated from tissue, as shown in FIGS. 11a and b. Cutting elements 14, as shown in FIGS. 11a and b, are attached to the drive rod 22 at a joint 18 that provides a link allowing the bending of the cutting element 14 as the drive rod 22 is rotated. By rotating the drive rod 22, the cutting element 14 contacts the side of the window 16 towards which the cutting element is rotated. The support structure 42 of the window 16 deflects the cutting element such that the cutting element follows the inner surface geometry of the catheter body 20. After the cutting element has been rotated completely within the catheter body, as shown in FIG. 11b, the cutting element is isolated from tissue enabling the manipulation of the catheter within the vasculature without damaging the anatomy. To deploy the cutting element, as shown in FIG. 11a, the drive rod 22 is rotated in the opposite direction. As the cutting element enters the region defined by the window, the cutting element deploys into an expanded configuration such that the cutting element contacts tissue adjacent to the window. This embodiment for deploying a cutting element has more controllability in deploying the cutting element. Of course, the rotatable drive rod may also be used to advance and retract the rotatable cutting element within the window to further increase the length of the thin, linear channels. As shown in FIGS. 6a to c, multiple cutting elements may be attached to a single drive rod so rotation of the drive rod compresses and deploys the multiple cutting elements. Alternatively, the multiple cutting elements may be attached to multiple drive rods.

The window 16 described above may be created with the opening extending through a larger angle relative to the catheter axis. In this configuration, the rotatable drive rod permits rotation of the cutting element along a greater angle producing thin, linear channels whose length extends perpendicular to the catheter axis. In this embodiment, the cutting element is fabricated such that the at least one cutting edge (and electrode when coagulation of tissue is employed) is located on at least one side of the cutting element. Therefore, rotation of the cutting element relative to the catheter axis cuts (and coagulates when electrodes are used) tissue extending throughout the angle defined by the window opening. In this later configuration, the axial length of the window is limited to prevent axial movement of the cutting element so the geometry of the channel is still a line.

As shown in FIGS. 11a and b, at least one signal wire 32 can be attached to the rotatable cutting elements to enable cauterization and/or coagulation of tissue adjacent to the cutting element. In this embodiment, the at least one signal wire 32 is wound around the drive rod 22 into a helix so excess tension is not exerted on the signal wire as the cutting element is rotated.

The cutting elements that do not need to be compressed in length to reduce the diameter, such as those in FIGS. 11a and b that are rotated to compress into a reduced diameter (as described previously) may be fabricated from a flat sheet cut into the desired pattern using chemical etching, laser cutting, wire EDM, waterjet cutting, or other manufacturing process. The edges may be ground into a sharp edge to enhance the cutting potential of the cutting element.

The inventions described in this patent application describe embodiments that permit controllably cutting a depth of tissue, mechanically and/or electrically. Embodiments of the invention that simultaneously coagulate and cut tissue utilize localized transmission of energy to precisely heat the endocardial surface, a cutting element to incise the heated tissue, and a support structure to maintain contact between the cutting element and tissue. An important feature to cutting and coagulating tissue is the current density profile emanating from an electrode into tissue. The configurations of the electrodes, shown in FIGS. 7a–e, make them more effective at simultaneously cutting and coagulating tissue. These electrodes are designed with distinct edges. These edges may be fabricated by laser drilling, wire EDM, mulling, grinding, or other manufacturing process. Deposited electrodes, when used, may be applied in patterns that contain numerous edges. When radiofrequency energy is transmitted to these electrodes, the edges produce high current densities that locally heat the vessel wall. The small cross-sectional diameters of the conductive material forming the electrodes ensures minimal depth of penetration, focuses heating of adjacent tissue, and helps to prevent damage to adjacent anatomy. Instead of requiring an extremely sharp cutting element, greater levels of energy transmission may be used to cauterize the tissue and produce the channel.

A large surface area indifferent ground pad may be placed on the patient's back, thigh, or other location and serve as the return path so radiofrequency energy may be delivered in a unipolar configuration. Alternatively, energy may be delivered bipolar between separate electrode pairs.

When the cutting element(s) act as electrodes, they may also be used to confirm contact between the cutting element and the endocardial surface by comparing the impedance between the electrode cutting element and a return path (indifferent patch electrode or second cutting element electrode). When the cutting element electrode(s) only contact blood, the impedance is substantially higher than when a portion of the cutting element electrode(s) contact the endocardial surface.

The catheter of the invention 10 is fabricated from a biocompatible polymer such as polyether block amide (Pebax), polyurethane (Pellethane), polyethylene, polyimide, or a combination of these or other materials. The polymer may incorporate a braided, woven, wound or other layer (or layers) of a reinforcing polymer, metal, fabric, or combination of aforementioned materials for increased torque control. The catheter body 20 may include barium sulfate, bismuth trioxide, tantalum, or other radiopaque substance to increase the visibility using fluoroscopy. The catheter of the invention 10 may have an outer diameter, with the cutting element and the support strands compressed into a reduced diameter, between 3 French and 15 French. The catheter may be fabricated from multiple lumen tubing using known manufacturing processes or may be fabricated from a single lumen tubing and having separate smaller tubings to isolate various functional elements of the catheter. The various lumens of the multiple lumen tubing or smaller tubings serve as the passages for the drive rod(s) and stylets.

The lumens connect to ports 48, 50, and 52 attached to the handle 34. The ports may be used to flush the lumens with heparinized saline to prevent clotting within the lumens. In addition, the ports may be used to inject therapeutic agents having various purposes. For example, the port 48 connecting to the lumen that is routed to at least one window and may be used for injecting angiogenic substances such as genetic solutions, hormones (e.g. estrogen), or other drug solutions into the channels created with the at least one cutting element. Gene therapy and the introduction of growth factors have been shown to accelerate and/or augment the angiogenic response. The introduction of therapeutic agents directly into the channels may be enhanced when electrodes are used to coagulate tissue. During the coagulation process, the energy transmitted into the myocardium produces electroporation of cell membranes and/or heats the tissue to also produce poration of cell membranes. By opening cell membranes, therapeutic agents more readily and rapidly diffuse into the cells accelerating the cellular response to the therapeutic agents.

Of particular interest is the cutting element 14 embodiment capable of directly injecting therapeutic agents (e.g. genetic solutions, growth factors, or other) into the channel while creating the channel. To accomplish this, the mechanical cutting element or cutting element with electrode is created from a metallic tube with holes 64 strategically positioned at an edge or tip designed to cut into a depth of tissue, as shown in FIG. 12. The holes 64 enable injecting the therapeutic solution from the cutting element (or electrode) into the incised tissue helping to enhance the angiogenic response. The hypotube is preferably fabricated from a memory elastic material such as nickel titanium or spring stainless steel and is thermally formed into the desired configuration; therefore, the cutting element can also function as the electrode. The hypotube may be fabricated with an edge on at least one side to act as a cutting element, as a flat sheet with an inner lumen to function as a cutting element and provide a lumen to inject therapeutic agents, or other cross-section. The hypotube may also have a conductive coating applied using materials and processes previously described. Any sharp edges would be incorporated in the electrode. The holes 64 are created through the sidewall of the hypotube using laser drilling, milling, wire EDM, or other fabrication methods. The proximal end of the hypotube is connected to a port in the handle providing a conduit to inject the desired therapeutic agent The hypotube may also function as the drive rod 22 to manipulate the cutting element.

Angiogenic substances include, but are not limited to, Vascular Endothelial Growth Factor (VEGF), Fibroblast Growth Factor (FGF), Epidermal Growth Factor (EGF), estrogen, and gene therapy compounds. The angiogenic substance can be contained in a fluid or biodegradable material such as a hydrogel or biodegradable polymer. Additional carriers for the angiogenic substances may include adhesives, gelatins, collagens, glycerol as well as other biocompatible, viscosity-enhancing materials. The carrier may also include a radiopaque material, allowing visualization of channel depth and position, as well as confirmation of the application of the angiogenic substance.

The holes 64 in the cutting element may additionally be used to inject cooled saline or other solution designed to prevent immediate coagulation of blood during radiofrequency energy delivery. This also prevents damage to adjacent tissue by cooling the tissue below the temperatures at which the myocytes become nonviable.

The catheter handle 34 may be fabricated from polycarbonate, polyethylene, PEEK, urethane or other material and may be injection molded, adhesively bonded, or thermally bonded to the catheter tubing 20. The handle 34 contains a knob 36 or slide mechanism attached to a movable drive rod 22 that passes through the handle and through a lumen fabricated in the catheter tubing. The handle 34 of the catheter also contains at least one actuator 44 connected to the at least one support strand 12. At least one stylet 26 connects the at least one actuator 44 to the at least one support strand 12 and passes through at least one lumen fabricated in the catheter tubing. Hemostatic valves constructed of silicone or other material having a large percent elongation characteristic may be used to prevent backflow of blood through the catheter lumens.

Another feature, which may be included in the catheter, is the inclusion of unidirectional or bi-directional steering. A steering mechanism 68 may be positioned within the catheter, as shown in FIGS. 11a and b. Typically, the steering mechanism may include a pullwire terminating at a flat spring or collar. The steering system has a more flexible distal section compared to the proximal tube body. When tension is placed on the pullwire, the catheter is deflected into a curve, which helps direct the catheter within the heart chamber. The pullwire may be wound, crimped, spot welded or soldered to the flat spring or collar placed in the catheter. This provides a stable point within the catheter for the pullwire to exert tensile force thus steer the catheter. The proximal tube body of the catheter may be reinforced by incorporating a helically wound wire within the catheter tubing extrusion to provide column support from which to better deflect the distal section. Alternatively, the steering mechanism 68 may consist of a superelastic material having a desired three-dimensional geometric shape at its distal end and sufficient rigidity to impart this shape in the catheter. By retracting the preformed steering wire 68 into the stiffer proximal section of the catheter, the distal end of the catheter straightens. Extending the preformed steering wire 68 into the more flexible distal section of the catheter causes the distal section to assume the shape of the steering wire. Alternatively, a catheter with a curved section can incorporate a tube or rod that can be advanced through that section to straighten it.

An additional feature that may be incorporated in the catheter is a preformed shape in the distal section of the catheter. The distal section may be preformed into a curve that biases the catheter to maximize tissue contact when the catheter is positioned into the appropriate heart chamber, and/or facilitate deploying the support strands from the catheter. This curve may consist of a single arc or a nonlinear geometry, such as an "S". A preshaped rod, hypotube, wire or coil, created from a memory elastic material such as nickel titanium or spring steel may be thermally formed into the desired geometry, and inserted into the distal section of the catheter during manufacturing or advanced through a dedicated lumen while the catheter is positioned in the vasculature of the body. The shaped wire may be attached to the distal tip of the catheter for those non-removable preshaped rods and secured to the handle of the catheter at its proximal end to provide a reinforcing structure throughout the entire length of the catheter. The catheter body may also or alternatively be thermally formed into a desired geometry.

The embodiments of the invention may also create thin, linear channels 8 from a coronary artery and into the myocardium. As shown in FIG. 12, the catheter may be positioned into a coronary artery (e.g. left anterior descending artery, circumflex artery, or right coronary artery) and used to create thin, linear channels through the coronary artery wall 7, past the epicardium, and into the myocardium 1. Once positioned within the coronary artery 7, the window(s) 16 of the catheter are oriented so they face the myocardium. Once positioned, support stands 12 may be deployed to urge the window(s) 16 of the catheter against the coronary artery wall 7. Then, the cutting element 14 is deployed, as previously discussed, and creates a thin, linear channel 8 mechanically and/or electrically. Once the channel is created into the myocardium, the catheter may be used to extend the channel longitudinally. As such blood flow may be re-routed through the channel and around lesions located in the coronary artery. This, accompanied by angiogenesis induced in the myocardium, increases blood flow to the myocardium.

Figure 1A:
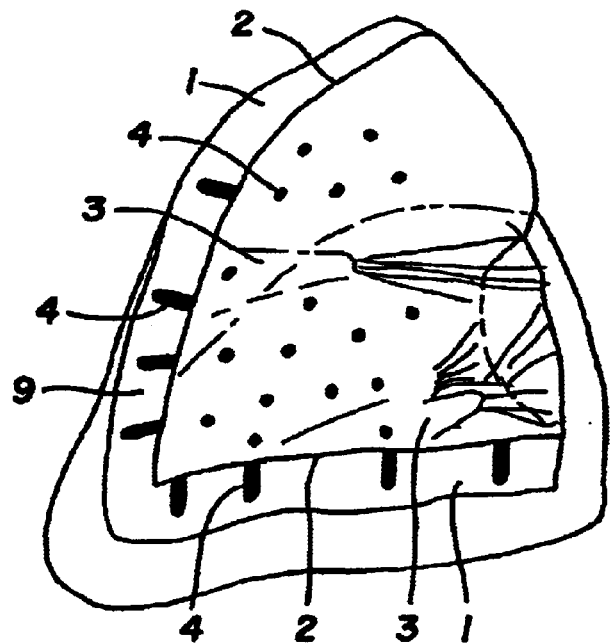
FIG. 1a shows a heart wall containing multiple channels created by a conventional percutaneous transmyocardial revascularization device.
Figure 1B:
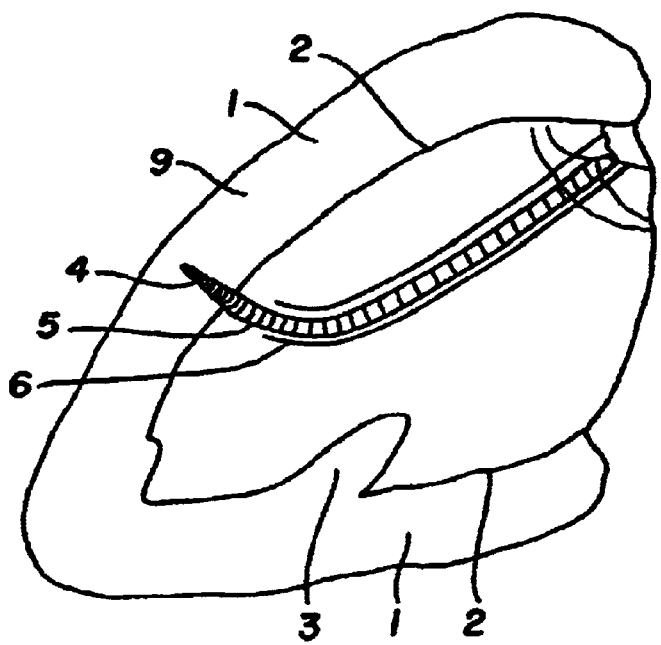
FIG. 1b illustrates the operation of the conventional percutaneous transmyocardial revascularization device.

A salient feature of the present invention is that elongate incisions, formed according to the present invention, more effectively and more rapidly treat a given area of myocardial tissue. FIG. 13 illustrates several rows and columns of bores 4 formed using a catheter distal tip, as illustrated in prior art FIG. 1b. In contrast, FIG. 14 illustrates a similarly sized area of cardiac tissue in which elongate, narrow and linear incisions have been formed in accordance with the present invention. The incisions 8 can be formed up to about 5 cm in length, but typically are considerably shorter, e.g. about 1 cm, while the incision width is preferably at most about 1 mm. Adjacent bores 4 are spaced approximately 5 mm from one another. Similarly, incisions 8 are separated from one another by about 5 mm, in both the axial and transverse directions. Because of its axial length, each incision 8 replaces several bores 4, leading to a more efficient (reduced time) treatment. The efficiency can be further enhanced if each axial column of incisions 8 is formed by a single catheter having several tissue cutting elements.

Another advantage is the improved depth control arising from the combination of the lengthwise or sideways disposition of the catheter along the endocardial surface and the use of strands 12 to urge the catheter surface against the endocardial surface where the incisions are formed. In contrast, controlling the depth of bores 4 with a catheter distal tip is considerably more difficult and yields a less repeatable, less uniform result. Further, the sideways positioning of the catheter pursuant to the invention is compatible with providing an atraumatic distal catheter tip, while such distal tip is incompatible with use of the tip to form bores 4. With respect to the use of a laser to form the bores, the present catheter affords the further advantage of the ability to control the degree of heat, if any, provided through a cutting element/electrode. In contrast to the ability to control the amount of current and therefore the amount of heat, e.g., to obtain a temperature above normal body temperature (for example 60 degrees C) in tissue surrounding the tissue cutting element, the laser is either on (i.e., hot) or off.

Another application for the mechanical and/or electrical axial cutting catheter is for the treatment of monomorphic or polymorphic ventricular tachycardia, or the prevention of ventricular fibrillation. Creating lines of subendocardial cuts defines a section of tissue that is electrically separated along the tissue plane. As such slow zones that travel along the endocardium from one region of the infarct border zone to another region are isolated from the remainder of the heart preventing the induction of ventricular tachycardia In addition, lines of cuts strategically positioned subendocardially and extending from the apex of the heart toward the mitral valve annulus directs the propagation throughout the heart and prevents wavelets from developing which may disrupt the rhythm. These cuts additionally encourage angiogenesis and limit the amount of myocardium damaged so the extremely wide lesions typical of conventional catheters may be avoided. As such these cuts should provide superior hemodynamics than similar lesions created with conventional catheters. In addition, these cutting catheters are capable of penetrating deep into the myocardium to target ventricular tachycardia substrates that are intramurally or subepicardially located.

Another application for the catheter of this invention is for the treatment of atrial fibrillation. In this application, a circumferential ablation or cut is formed e.g. in the pulmonary vein to isolate the electrical propagation of tissue in the vein from the atrium. Such circumferential ablation (and cut as well, if desired) is effected by positioning the catheter in the pulmonary vein, advancing one or more heating elements (for cutting if desired) from one or more locations on the catheter body, and rotating the catheter through a desired arcuate length, preferably at least one rotation. In this application a resistive heating element advantageously affords temperature control to avoid vessel contraction (e.g. at 70 degrees C).

Finally, while the foregoing description is focused primarily on endocardial cutting, the cutting mechanisms of this invention can be incorporated into handheld devices and used to create thin, linear elongate incisions on the epicardial surface or other surfaces accessible through the thoracic cavity, the abdominal cavity, or other region external to a body organ.

Although the present invention has been described in terms of the preferred embodiments above, numerous modifications and/or additions to the above-described preferred embodiments within the scope of this invention will be readily apparent to one skilled in the art.

What is claimed is:

1. A device for performing percutaneous transmyocardial revascularization, including:

an elongate catheter having a proximal end and a distal end, a catheter wall defining a compartment within the catheter, and at least one window through the catheter wall open to the compartment;

a cutting element compressible into a reduced diameter when positioned within the compartment and tending to radially expand beyond the catheter wall when positioned near the at least one window; and a control component coupled to the cutting element and operable to selectively position and move the cutting element to a location near the window to allow said radial expansion through the window.

2. The device of claim 1 further including:

support strands adapted to be manipulated into contact with a first tissue surface to locate the at least one window against an opposing second tissue surface;

wherein the cutting edge, when radially expanded, cuts tissue along the second tissue surface.

3. The device of claim 1 wherein:

said tissue cutting element is electrically conductive, and coupled to an energy source comprising a means for generating an electrical current in the cutting edge to heat tissue adjacent the cutting edge at least to a temperature above normal body temperature.

4. The device of claim 3 wherein:

the energy source includes a power supply, an first and second electrical conductors coupled to the power supply and respectively to opposite ends of the cutting edge.

5. The device of claim 3 wherein:

the energy source includes a radiofrequency power source, an indifferent electrode, a first conductor connected to the radiofrequency power source and to the cutting element, and a second conductor connected to the radiofrequency power source and to the indifferent electrode, to maintain the adjacent tissue at least above normal body temperature.

6. The device of claim 1 including:

a component for urging the cutting element against tissue.

7. The device of claim 6 wherein:

the component for urging the cutting element includes at least one flexible support strand on the opposite side of catheter from the cutting element.

8. The device of claim 1 including:

a passage for delivering a therapeutic agent to tissue.

9. The device of claim 8 wherein:

the passage includes a lumen inside the cutting element; and the cutting element contains holes for injecting the therapeutic agent from inside the lumen to tissue adjacent the cutting element.

10. An elongate catheter for cutting incisions into heart tissue comprising:

at least one window through the catheter wall adapted to be positioned against a first tissue surface such that the at least one window faces the first tissue surface;

at least one support strand adapted to be manipulated into contact with a second tissue surface separate from the first tissue surface to force the at least one window into contact with the first tissue surface;

a cutting element that has a tendency to expand beyond the catheter wall when positioned near the at least one window to contact the first tissue surface when positioned near the at least one window such that the cutting element cuts tissue adjacent the at least one window to a predetermined depth determined by the shape of the cutting element; and a first control component coupled to the cutting element and operable to selectively position and move the cutting element along the at least one window.

11. The catheter of claim 10 further including:

a second control component coupled to the at least one support strand and operable to selectively position and move the at least one support strand into contact with the second tissue surface.

12. The catheter of claim 10 wherein:

said tissue cutting element includes an electrode adapted for a coupling to an energy source for generating an electrical current in the electrode to heat tissue adjacent the electrode at least to a temperature above normal body temperature.

13. The catheter of claim 12 wherein:

the energy source includes a power supply, and first and second electrical conductors coupled to the power supply and respectively to opposite ends of the electrode.

14. The catheter of claim 12 wherein:

the energy source includes a radiofrequency power source, an indifferent electrode, a first conductor connected to the radiofrequency power source and to the electrode, and a second conductor connected to the radiofrequency power source and to the indifferent electrode, to maintain the adjacent tissue at least above normal body temperature.

15. The catheter of claim 10 wherein:

the cutting element includes a lumen connected to a port near the proximal end of the catheter; and the cutting element further includes holes coupled to the lumen and adapted to pass a therapeutic agent from the port into tissue adjacent the cutting element.

16. The device of claim 10 wherein:

the cutting element is elastically compressible into a reduced diameter to facilitate catheter manipulation within the vasculature, and expandable back to a preformed shape when not constrained means.

17. The device of claim 10 wherein:

the cutting element is shaped to form incisions having a length at least twice an incision width.

18. The device of claim 10 wherein:

the incisions have a length that is greater than their depth.

19. A process for performing transmyocardial revascularization including:

positioning a catheter incorporating at least one window through the catheter wall into contact with an endocardial surface such that the at least one window faces the endocardial surface; and using a cutting element projecting through the window to form at least one incision through the endocardial surface to a depth within the myocardium along a first line, wherein the cutting element has a tendency to expand beyond the catheter wall when positioned near the at least one window and the at least one incision has a length substantially greater than its width and is positioned adjacent the at least one window with said length running substantially parallel to the endocardial surface.

20. The process of claim 19 further including:

positioning the catheter in contact with the endocardial surface along a second line spaced apart from the first line; and creating at least one incision along the second line.

21. The process of claim 19 wherein:

at least two incisions are created along the first line; and the at least two incisions are separated by a gap of uncut endocardium.

22. The process of claim 19 further including:

injecting a therapeutic agent directly into the at least one incision.

23. The process of claim 19 wherein:

the at least one incision has a length that is at least twice as large as a width of the incision.

24. The process of claim 19 wherein:

the at least one channel has a length that is greater than a depth of the incision.

25. The process of claim 19 wherein:

positioning the at least one window includes extending at least one flexible support strand into contact with the endocardial surface to urge the at least one window into contact with the endocardial surface along the first line.

26. A process for treating myocardial tissue, including:

maneuvering a catheter intravascularly to position a distal end region of the catheter inside the heart;

selectively positioning the catheter such that the distal end region of the catheter extends axially along the endocardial surface; and with the catheter so positioned, causing or allowing a cutting element extended axially along said distal region of the catheter to project radially outwardly from the catheter and through the endocardial surface into myocardial tissue, thus to form an incision in the myocardial tissue having an axial length at least twice its width, wherein the cutting element has a tendency to expand beyond the catheter.

27. The process of claim 26 further including:

urging the catheter distal region against the endocardial sure during said projecting of the cutting element.

28. The process of claim 26 wherein:

said projecting the cutting element is accomplished with minimal arcuate movement of the cutting element, and the cutting element is elongate in the axial direction, whereby the incision has an incision width substantially equal to a cutting-element width.

29. The process of claim 28 wherein:

the incision has a length in the axial direction at least ten times the width.

* * * * *